US010667868B2

(12) United States Patent
Malackowski

(10) Patent No.: US 10,667,868 B2
(45) Date of Patent: Jun. 2, 2020

(54) SYSTEM AND METHODS FOR PERFORMING SURGERY ON A PATIENT AT A TARGET SITE DEFINED BY A VIRTUAL OBJECT

(71) Applicant: Stryker Corporation, Kalamazoo, MI (US)

(72) Inventor: Donald W. Malackowski, Schoolcraft, MI (US)

(73) Assignee: Stryker Corporation, Kalamazoo, MI (US)

( * ) Notice: Subject to any disclaimer, the term of this patent is extended or adjusted under 35 U.S.C. 154(b) by 539 days.

(21) Appl. No.: 15/393,876

(22) Filed: Dec. 29, 2016

(65) Prior Publication Data
US 2017/0189125 A1 Jul. 6, 2017

Related U.S. Application Data

(60) Provisional application No. 62/273,543, filed on Dec. 31, 2015.

(51) Int. Cl.
*A61B 34/20* (2016.01)
*A61B 34/30* (2016.01)
(Continued)

(52) U.S. Cl.
CPC .............. *A61B 34/20* (2016.02); *A61B 5/065* (2013.01); *A61B 34/30* (2016.02); *A61B 90/361* (2016.02);
(Continued)

(58) Field of Classification Search
CPC ......... A61B 19/00; A61B 17/16; A61B 17/02; A61B 34/32; A61B 34/30; A61B 90/03;
(Continued)

(56) References Cited

U.S. PATENT DOCUMENTS 4,962,463 A  10/1990 Crossno et al.
5,603,318 A  2/1997 Heilbrun et al.
(Continued)

FOREIGN PATENT DOCUMENTS

DE  19639615 C2  10/1999
EP  0685088 B1  9/2000
(Continued)

OTHER PUBLICATIONS

International Search Report for Application No. PCT/US2016/069152 dated Apr. 6, 2017, 2 pages.
(Continued)

*Primary Examiner* — Carl H Layno
*Assistant Examiner* — Jon Eric C Morales
(74) *Attorney, Agent, or Firm* — Howard & Howard Attorneys PLLC

(57) ABSTRACT

System and methods for performing surgery at a target site defined by a virtual object. A surgical navigation system includes a patient tracker to be attached to a patient. A localizer cooperates with the patient tracker and generates localizer data associated with the target site during the surgery. The surgical navigation system also includes a vision device to generate image data associated with the target site and surfaces surrounding the target site. A navigation computer in communication with the localizer and the vision device is configured to determine a region to be avoided outside of the target site based on the localizer data and the image data. In some cases, a second virtual object is generated to define the region to be avoided so that a surgical instrument used during the surgery avoids the region.

12 Claims, 5 Drawing Sheets

(51) Int. Cl.
*A61B 90/00* (2016.01)
*A61B 5/06* (2006.01)
*A61B 17/00* (2006.01)

(52) U.S. Cl.
CPC .............. *A61B 2017/00734* (2013.01); *A61B 2034/2048* (2016.02); *A61B 2034/2051* (2016.02); *A61B 2034/2055* (2016.02); *A61B 2034/2068* (2016.02); *A61B 2034/2072* (2016.02); *A61B 2090/364* (2016.02); *A61B 2090/3937* (2016.02); *A61B 2090/3945* (2016.02)

(58) Field of Classification Search
CPC .......... A61B 34/20; A61B 2017/00734; A61B 2034/2055; A61B 2090/3983; A61B 2034/2048; A61B 2034/2068; A61B 2090/3945; A61B 2034/2061; A61B 2090/3937; Y10S 901/09; Y10S 901/47
USPC ........................................................ 606/130
See application file for complete search history.

(56) References Cited

U.S. PATENT DOCUMENTS

| | | | |
|---|---|---|---|
| 5,715,836 | A | 2/1998 | Kliegis et al. |
| 5,765,561 | A | 6/1998 | Chen et al. |
| 5,817,005 | A | 10/1998 | Cohen |
| 6,021,343 | A | 2/2000 | Foley et al. |
| 6,236,875 | B1 | 5/2001 | Bucholz et al. |
| 6,434,507 | B1 | 8/2002 | Clayton et al. |
| 6,450,978 | B1 | 9/2002 | Brosseau et al. |
| 6,511,418 | B2 | 1/2003 | Shahidi et al. |
| 6,724,922 | B1 | 4/2004 | Vilsmeier |
| 6,757,416 | B2 | 6/2004 | Kleiman et al. |
| 6,815,659 | B2 | 11/2004 | Cartlidge |
| 6,850,794 | B2 | 2/2005 | Shahidi |
| 6,858,003 | B2 | 2/2005 | Evans et al. |
| 6,929,606 | B2 | 8/2005 | Ritland |
| 6,951,538 | B2 | 10/2005 | Ritland |
| 7,043,961 | B2 | 5/2006 | Pandey et al. |
| 7,050,845 | B2 | 5/2006 | Vilsmeier |
| 7,166,114 | B2 | 1/2007 | Moctezuma De La Barrera et al. |
| 7,492,930 | B2 | 2/2009 | Leitner et al. |
| 7,561,733 | B2 | 7/2009 | Vilsmeier et al. |
| 7,630,753 | B2 | 12/2009 | Simon et al. |
| 7,725,162 | B2 | 5/2010 | Malackowski et al. |
| 7,726,564 | B2 | 6/2010 | Goldbach |
| 7,747,312 | B2 | 6/2010 | Barrick et al. |
| 7,801,342 | B2 | 9/2010 | Boese et al. |
| 7,840,253 | B2 | 11/2010 | Tremblay et al. |
| 7,967,742 | B2 | 6/2011 | Hoeg et al. |
| 7,987,001 | B2 | 7/2011 | Teichman et al. |
| 8,027,526 | B2 | 9/2011 | Boese et al. |
| 8,041,459 | B2 | 10/2011 | Sutherland et al. |
| 8,187,180 | B2 | 5/2012 | Pacey |
| 8,320,612 | B2 | 11/2012 | Knobel et al. |
| 8,343,048 | B2 | 1/2013 | Warren, Jr. |
| 8,382,372 | B2 | 2/2013 | Maschke |
| 8,442,621 | B2 | 5/2013 | Gorek et al. |
| 8,792,963 | B2 | 7/2014 | Zhao et al. |
| 8,838,205 | B2 | 9/2014 | Shoham et al. |
| 8,945,140 | B2 | 2/2015 | Hubschman et al. |
| 8,954,132 | B2 | 2/2015 | Hubschman et al. |
| 8,974,380 | B2 | 3/2015 | Michaeli et al. |
| 9,002,432 | B2 | 4/2015 | Feilkas |
| 9,008,757 | B2 | 4/2015 | Wu |
| 9,044,257 | B2 | 6/2015 | Fielding et al. |
| 9,119,655 | B2 | 9/2015 | Bowling et al. |
| 9,119,670 | B2 | 9/2015 | Yang et al. |
| 9,168,104 | B2 | 10/2015 | Dein |
| 9,188,973 | B2 | 11/2015 | Tenney et al. |
| 9,283,048 | B2 | 3/2016 | Kostrzewski et al. |
| 9,307,969 | B2 | 4/2016 | Novak et al. |
| 9,402,691 | B2 | 8/2016 | Merritt et al. |
| 9,420,944 | B2 | 8/2016 | Sutherland et al. |
| 9,492,240 | B2 | 11/2016 | Itkowitz et al. |
| 9,510,771 | B1 | 12/2016 | Finley et al. |
| 9,510,914 | B2 | 12/2016 | Yang et al. |
| 9,542,743 | B2 | 1/2017 | Tenney et al. |
| 9,566,052 | B2 | 2/2017 | Novak |
| 9,603,665 | B2 | 3/2017 | Bowling et al. |
| 9,629,595 | B2 | 4/2017 | Walker et al. |
| 9,642,606 | B2 | 5/2017 | Charles et al. |
| 9,668,819 | B2 | 6/2017 | Stolka et al. |
| 9,681,796 | B2 | 6/2017 | Tesar et al. |
| 9,718,190 | B2 | 8/2017 | Larkin et al. |
| 9,733,336 | B2 | 8/2017 | Shen et al. |
| 9,733,463 | B2 | 8/2017 | Eslami et al. |
| RE46,562 | E | 10/2017 | Huennekens et al. |
| 9,833,254 | B1 | 12/2017 | Barral et al. |
| 9,867,531 | B2 | 1/2018 | Pacey et al. |
| 9,901,408 | B2 | 2/2018 | Larkin |
| 9,901,409 | B2 | 2/2018 | Yang et al. |
| 9,933,606 | B2 | 4/2018 | Saur et al. |
| 9,987,093 | B2 | 6/2018 | Christian et al. |
| 10,039,474 | B2 | 8/2018 | Taylor et al. |
| 10,045,882 | B2 | 8/2018 | Balicki et al. |
| 10,064,691 | B2 | 9/2018 | Frimer et al. |
| 10,154,882 | B2 | 12/2018 | Garbey et al. |
| 10,159,532 | B1 | 12/2018 | Ummalaneni |
| 10,165,981 | B2 | 1/2019 | Schoepp |
| 10,178,368 | B2 | 1/2019 | Zhao et al. |
| 10,247,545 | B2 | 4/2019 | Elliot |
| 2004/0010190 | A1 | 1/2004 | Shahidi |
| 2005/0054895 | A1 | 3/2005 | Hoeg et al. |
| 2005/0054897 | A1 | 3/2005 | Hashimoto et al. |
| 2005/0143651 | A1 | 6/2005 | Verard et al. |
| 2005/0203490 | A1 | 9/2005 | Simonson |
| 2006/0258938 | A1 | 11/2006 | Hoffman et al. |
| 2007/0135686 | A1 | 6/2007 | Pruitt et al. |
| 2007/0183637 | A1 | 8/2007 | Kreuzer et al. |
| 2008/0021283 | A1 | 1/2008 | Kuranda |
| 2008/0183068 | A1 | 7/2008 | Carls et al. |
| 2008/0200794 | A1 | 8/2008 | Teichman et al. |
| 2008/0243142 | A1 | 10/2008 | Gildenberg |
| 2008/0281989 | A1 | 11/2008 | Hager et al. |
| 2009/0024140 | A1 | 1/2009 | Allen et al. |
| 2009/0157059 | A1 | 6/2009 | Allen et al. |
| 2010/0295931 | A1 | 11/2010 | Schmidt |
| 2011/0075912 | A1 | 3/2011 | Rieber et al. |
| 2012/0190965 | A1 | 7/2012 | Schaerer et al. |
| 2014/0039681 | A1 | 2/2014 | Malackowski et al. |
| 2014/0107426 | A1 | 4/2014 | Wilson |
| 2014/0171787 | A1 | 6/2014 | Garbey et al. |
| 2014/0200621 | A1 | 7/2014 | Bowling et al. |
| 2014/0221822 | A1 | 8/2014 | Ehlers et al. |
| 2014/0276943 | A1* | 9/2014 | Bowling ................ A61B 17/16 606/130 |
| 2015/0005643 | A1 | 1/2015 | Whitman et al. |
| 2015/0018622 | A1 | 1/2015 | Tesar et al. |
| 2015/0265370 | A1 | 9/2015 | Garbey et al. |
| 2015/0351860 | A1 | 12/2015 | Piron et al. |
| 2016/0113728 | A1 | 4/2016 | Piron et al. |
| 2016/0183911 | A1 | 6/2016 | Waksman |
| 2016/0278864 | A1 | 9/2016 | Paitel |
| 2016/0345917 | A1 | 12/2016 | Daon et al. |
| 2017/0143429 | A1 | 5/2017 | Richmond et al. |
| 2017/0143432 | A1 | 5/2017 | Bowling et al. |
| 2017/0189125 | A1 | 7/2017 | Malackowski |
| 2017/0209225 | A1 | 7/2017 | Wu |
| 2017/0215857 | A1 | 8/2017 | D'Urso |
| 2017/0238998 | A1 | 8/2017 | Srimohanarajah et al. |
| 2017/0265947 | A1 | 9/2017 | Dyer et al. |
| 2017/0281282 | A1 | 10/2017 | Noonan et al. |
| 2017/0296162 | A1 | 10/2017 | Wan |
| 2017/0312036 | A1 | 11/2017 | Hoffman et al. |
| 2017/0325674 | A1 | 11/2017 | Kleiner et al. |
| 2017/0333137 | A1 | 11/2017 | Roessler |
| 2017/0358091 | A1 | 12/2017 | Ekin |
| 2018/0078315 | A1 | 3/2018 | Ren et al. |
| 2018/0116732 | A1 | 5/2018 | Lin et al. |
| 2018/0147727 | A1 | 5/2018 | Mewes et al. |

(56) References Cited

U.S. PATENT DOCUMENTS

| | | |
|---|---|---|
| 2018/0153626 A1 | 6/2018 | Yang et al. |
| 2018/0199951 A1 | 7/2018 | Chappuis et al. |
| 2018/0228553 A1 | 8/2018 | Bai et al. |
| 2018/0235715 A1 | 8/2018 | Amiot et al. |
| 2018/0303580 A1 | 10/2018 | Salah et al. |
| 2018/0311012 A1 | 11/2018 | Moctezuma et al. |
| 2018/0368929 A1 | 12/2018 | Popovic et al. |
| 2019/0050984 A1 | 2/2019 | Blendinger |
| 2019/0059833 A1 | 2/2019 | Govari |
| 2019/0069962 A1 | 3/2019 | Tabandeh et al. |

FOREIGN PATENT DOCUMENTS

| | | |
|---|---|---|
| EP | 1321105 B1 | 8/2003 |
| EP | 3449859 A1 | 3/2019 |
| WO | 2001003586 A1 | 1/2001 |
| WO | 2009045827 A2 | 4/2009 |
| WO | 2011134083 A1 | 11/2011 |
| WO | 2013132501 A1 | 9/2013 |
| WO | 2015100310 A1 | 7/2015 |
| WO | 2017012624 A1 | 1/2017 |
| WO | 2017059870 A1 | 4/2017 |
| WO | 2017158592 A2 | 9/2017 |
| WO | 2017187795 A1 | 11/2017 |
| WO | 2017195192 A1 | 11/2017 |
| WO | 2017205351 A1 | 11/2017 |
| WO | 2018237187 A2 | 12/2018 |
| WO | 2018237187 A3 | 1/2019 |
| WO | 2019070729 A1 | 4/2019 |
| WO | 2019070997 A1 | 4/2019 |

OTHER PUBLICATIONS

English language abstract and machine-assisted English translation for DE 196 39 615 extracted from espacenet.com database on Nov. 29, 2018, 26 pages.

English language abstract not found for EP 0 685 088; however, see English language equivalent U.S. Pat. No. 5,715,836. Original document extracted from espacenet.com database on Nov. 29, 2018, 13 pages.

English language abstract for EP 1 321 105 extracted from espacenet.com database on Nov. 29, 2018, 2 pages.

English language abstract for WO 2017/187795 extracted from espacenet.com database on Jun. 20, 2019, 2 pages.

\* cited by examiner

SYSTEM AND METHODS FOR PERFORMING SURGERY ON A PATIENT AT A TARGET SITE DEFINED BY A VIRTUAL OBJECT

RELATED APPLICATIONS

This application claims priority to and the benefit of U.S. Provisional Patent Application No. 62/273,543, filed Dec. 31, 2015, the entire contents and disclosure of which are hereby incorporated by reference herein.

TECHNICAL FIELD

The present disclosure relates generally to a system and method for performing surgery on a patient at a target site defined by a virtual object.

BACKGROUND

Navigation systems assist users in precisely locating objects. For instance, navigation systems are used in industrial, aerospace, and medical applications. In the medical field, navigation systems assist surgeons in precisely placing surgical instruments relative to a target site in a patient. The target site usually requires some form of treatment, such as tissue removal. In some cases, the target site is defined in the navigation system using a virtual object, such as a 3-D model. A representation of the virtual object can be displayed to the user during surgery to assist the user in visualizing placement of a treatment end of the instrument relative to the target site. For instance, the target site may be associated with a bone of the patient and the virtual object may define a volume of the bone to be removed by the treatment end of the instrument.

Conventional navigation systems employ a localizer that cooperates with trackers to provide position and/or orientation data associated with the instrument and the target site, e.g., the volume of the bone to be removed. The localizer is usually placed so that it has a field of view of the trackers. The trackers are fixed to the instrument and to the patient to move in concert with the instrument and the patient. The tracker attached to the patient is attached to the bone being treated thereby maintaining a rigid relationship with respect to the target site owing to the rigid nature of the bone. By using separate trackers on the instrument and the patient, the treatment end of the instrument can be precisely positioned to stay within the target site.

Often, the target site is located adjacent to sensitive anatomical structures, such as soft tissue, that should be avoided during surgery. These sensitive anatomical structures are difficult to track using conventional trackers, as these sensitive anatomical structures can shift relative to the trackers due to their elastic and/or flexible nature. Just as often, retractors or other tools are located near the target site that should also be avoided during the surgery. The retractors or other tools could be tracked in the same manner as the instrument being used for treating the patient, but adding trackers to the retractors and other tools can substantially increase costs and complexity in the navigation system, particularly by increasing the number of objects to be tracked by the navigation system. As a result, in current surgical procedures, avoidance is sometimes the responsibility of the user, so extreme care must be taken by the user to avoid sensitive anatomical structures and untracked tools that may be near the target site.

Thus, there is a need in the art for navigation systems and methods that address the identification of sensitive anatomical structures and/or other structures that are to be avoided during surgery.

SUMMARY

In one embodiment, a surgical navigation system for performing surgery at a target site defined by a virtual object is provided. The surgical navigation system includes a patient tracker to be attached to a patient. A localizer cooperates with the patient tracker and generates localizer data associated with the target site during the surgery. The surgical navigation system also includes a vision device to generate image data associated with the target site and surfaces surrounding the target site. A navigation computer in communication with the localizer and the vision device is configured to determine a region to be avoided outside of the target site based on the localizer data and the image data.

In another embodiment, a robotic surgical system for performing surgery at a target site defined by a virtual object is provided. The robotic surgical system includes a robotic device. An end effector is coupled to the robotic device for treating the target site. The robotic surgical system also includes a patient tracker to be attached to a patient. A localizer cooperates with the patient tracker and generates localizer data associated with the target site during the surgery. The robotic surgical system includes a vision device to generate image data associated with the target site and surfaces surrounding the target site. A navigation computer in communication with the localizer and the vision device is configured to determine a region to be avoided outside of the target site during the surgery based on the localizer data and the image data. The navigation computer is in communication with the robotic device so that the robotic device is operable to move the end effector with respect to the target site while avoiding the region to be avoided.

In another embodiment, a method of performing surgery at a target site defined by the virtual object is provided. The method comprises generating localizer data associated with the target site while a patient tracker is attached to a patient. Image data associated with the target site and surfaces surrounding the target site is also generated. The method further comprises determining a region to be avoided outside of the target site during the surgery based on the localizer data and the image data.

These systems and methods provide several advantages. For instance, by capturing both localizer data using the localizer and image data using the vision device, the navigation computer is able to identify the region to be avoided that is located outside of the target site. As a result, these systems and methods, in some embodiments, provide for accurate placement of surgical instruments to avoid sensitive anatomical structures that are otherwise difficult to track and to avoid other tools near the target site that may not be outfitted with separate trackers.

BRIEF DESCRIPTION OF THE DRAWINGS

Advantages will be readily appreciated as the same becomes better understood by reference to the following detailed description when considered in connection with the accompanying drawings.

DETAILED DESCRIPTION

Figure 1:
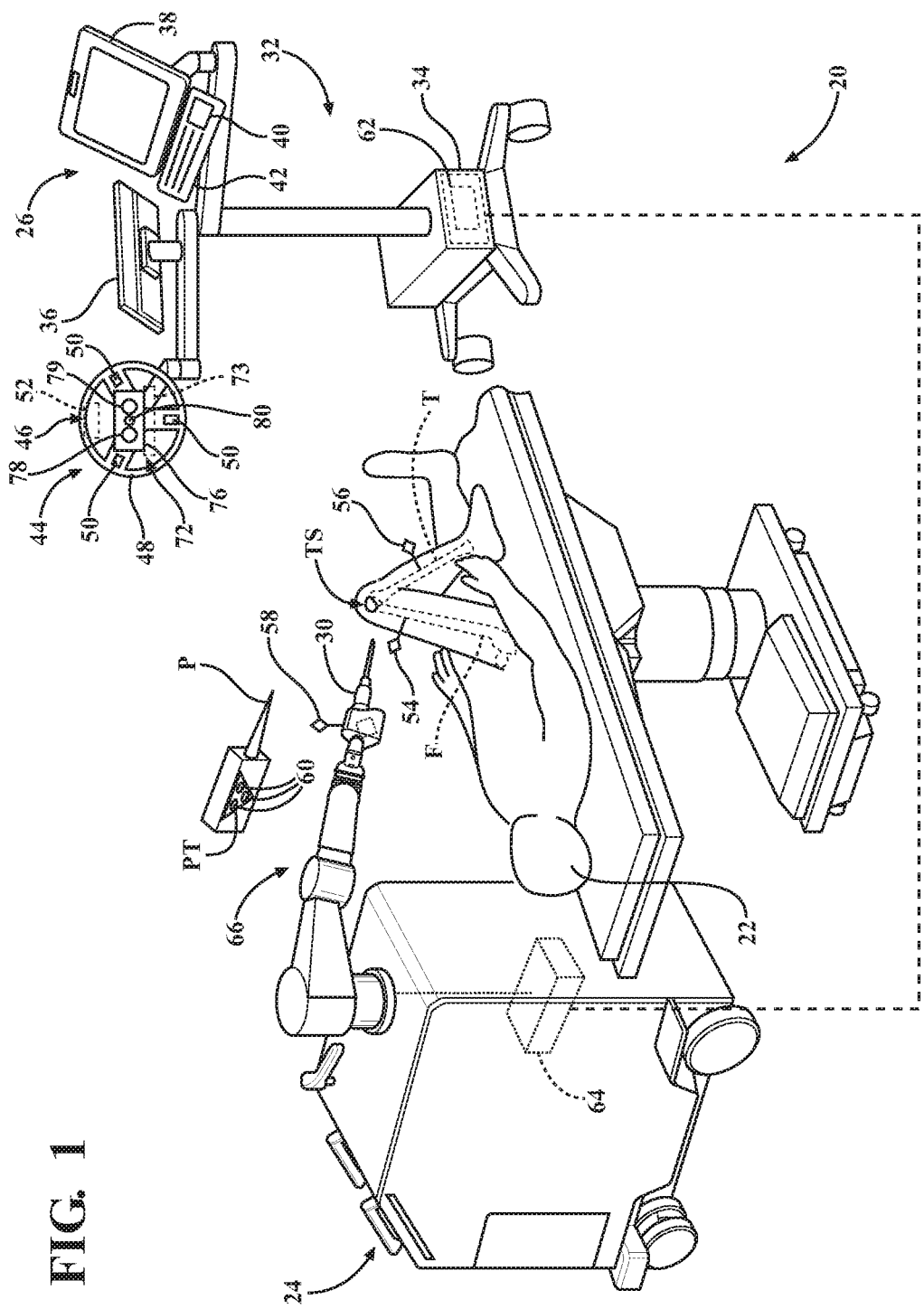
FIG. 1 is a perspective view of a robotic surgical system comprising a localizer and a vision device.

As shown in FIG. 1, a system 20 for treating a patient 22 is illustrated. The system 20 is shown in a surgical setting such as an operating room of a medical facility. In the embodiment shown, the system 20 comprises a machining station 24 and a guidance station 26. The guidance station 26 is set up to track movement of various objects in the operating room. Such objects include, for example, a surgical instrument 30, a femur F of a patient, and a tibia T of the patient. The guidance station 26 tracks these objects for purposes of displaying their relative positions and orientations to a user and, in some cases, for purposes of controlling or constraining movement of the surgical instrument 30 relative to target sites. The surgical instrument 30 is shown as part of the machining station 24. However, in other embodiments, the surgical instrument 30 is manually held and moved by the user.

The target sites to be treated by the surgical instrument 30 are defined by virtual objects. In the embodiment shown, a femur target site TS is shown, which is associated with the femur F. Of course, several other target sites, such as a target site for the tibia T, are also possible, with each being defined by its own separate virtual object. The virtual objects representing the target sites are pre-operatively set by the user and/or automatically generated to define volumes of material to be treated, trajectories for the surgical instrument 30, planes to be cut by the surgical instrument 30, bores to be drilled, and the like. In the embodiment shown, a virtual object VB (see FIG. 4) defines the volume of material to be removed from the femur F. In some cases, the virtual objects are set or re-set intraoperatively, i.e., during the surgical procedure. It should be appreciated that although the description set forth herein relates to orthopedic surgical procedures, the systems and methods described herein are likewise suitable for any type of surgical procedure.

The guidance station 26 includes a navigation cart assembly 32 that houses a navigation computer 34. A navigation interface is in operative communication with the navigation computer 34. The navigation interface includes a first display 36 adapted to be situated outside of the sterile field and a second display 38 adapted to be situated inside the sterile field. The displays 36, 38 are adjustably mounted to the navigation cart assembly 32. First and second input devices 40, 42 such as a keyboard and mouse can be used to input information into the navigation computer 34 or otherwise select/control certain aspects of the navigation computer 34. Other input devices are contemplated including a touch screen (not shown) or voice-activation.

A localizer 44 communicates with the navigation computer 34. In the embodiment shown, the localizer 44 is an optical localizer and includes a localizer camera unit 46. The localizer camera unit 46 has an outer casing 48 that houses one or more optical position sensors 50. In some embodiments at least two optical sensors 50 are employed, preferably three, four, or more. The optical sensors 50 may be three separate charge-coupled devices (CCD). In one embodiment three, one-dimensional CCDs are employed. It should be appreciated that in other embodiments, separate localizer camera units, each with a separate CCD, or two or more CCDs, could also be arranged around the operating room. The CCDs detect infrared signals. Additionally, the localizer 44 may employ different modalities and may be an electromagnetic localizer, RF localizer, ultrasound localizer, or any other conventional localizer capable of tracking objects.

The localizer camera unit 46 is mounted to an adjustable arm to position the optical sensors 50 with a field of view of the below discussed trackers that, ideally, is free from obstructions. In some embodiments the localizer camera unit 46 is adjustable in at least one degree of freedom by rotating about a rotational joint. In other embodiments, the localizer camera unit 46 is adjustable about two or more degrees of freedom.

The localizer camera unit 46 includes a localizer camera controller 52 in communication with the optical sensors 50 to receive signals from the optical sensors 50. The localizer camera controller 52 communicates with the navigation computer 34 through either a wired or wireless connection (not shown). One such connection may be an IEEE 1394 interface, which is a serial bus interface standard for high-speed communications and isochronous real-time data transfer. The connections could also use a company specific protocol. In other embodiments, the optical sensors 50 communicate directly with the navigation computer 34.

Position and orientation signals and/or data are transmitted to the navigation computer 34 for purposes of tracking objects. The navigation cart assembly 32, displays 36, 38, and localizer camera unit 46 may be like those described in U.S. Pat. No. 7,725,162 to Malackowski, et al. issued on May 25, 2010, entitled "Surgery System," hereby incorporated by reference.

Navigation computer 34 has the displays 36, 38, central processing unit (CPU) and/or other processors 62, memory (not shown), and storage (not shown) necessary for carrying out the functions described herein. The navigation computer 34 is loaded with software as described below. The software converts the signals received from the localizer camera unit 46 into localizer data representative of the position and orientation of the objects being tracked.

Guidance station 26 is operable with a plurality of tracking devices 54, 56, 58, also referred to herein as trackers. In the illustrated embodiment, one tracker is 54 is firmly affixed to the femur F of the patient and another tracker 56 is firmly affixed to the tibia T of the patient. Trackers 54, 56 are firmly affixed to sections of bone. Trackers 54, 56 may be attached to the femur F and tibia T in the manner shown in U.S. Pat. No. 7,725,162, hereby incorporated by references. Trackers 54, 56 could also be mounted like those shown in U.S. Patent Application Publication No. 2014/0200621, filed on Jan. 16, 2014, entitled, "Navigation Systems and Methods for Indicating and Reducing Line-of-Sight Errors," hereby incorporated by reference herein. In yet further embodiments, the trackers 54, 56 could be mounted to other tissues of the anatomy.

An instrument tracker 58 is firmly attached to the surgical instrument 30. The instrument tracker 58 may be integrated into the surgical instrument 30 during manufacture or may be separately mounted to the surgical instrument 30 in preparation for surgical procedures. A treatment end of the surgical instrument 30, which is being tracked by virtue of the instrument tracker 58, may be a rotating bur, electrical ablation device, or the like.

The trackers 54, 56, 58 can be battery powered with an internal battery or may have leads to receive power through the navigation computer 34, which, like the localizer camera unit 46, preferably receives external power.

In the embodiment shown, the surgical instrument 30 is attached to a manipulator 66 of the machining station 24. The manipulator 66 may also be referred to as a robotic device or a robotic arm. Such an arrangement is shown in U.S. Pat. No. 9,119,655, entitled, "Surgical Manipulator Capable of Controlling a Surgical Instrument in Multiple Modes," the disclosure of which is hereby incorporated by reference. It should be appreciated that in other embodiments, the surgical instrument 30 is manually manipulated without any robotic constraint on its position and/or orientation. The surgical instrument 30 may be any surgical instrument (also referred to as a tool) that is useful in performing medical/surgical procedures. The surgical instrument 30 may be a burring instrument, an electrosurgical instrument, an ultrasonic instrument, a reamer, an impactor, a sagittal saw, or other instrument. In some embodiments, multiple surgical instruments are employed to treat the patient, with each being separately tracked by the localizer 44.

The optical sensors 50 of the localizer 44 receive light signals from the trackers 54, 56, 58. In the illustrated embodiment, the trackers 54, 56, 58 are active trackers. In this embodiment, each tracker 54, 56, 58 has at least three active tracking elements or markers for transmitting light signals to the optical sensors 50. The active markers can be, for example, light emitting diodes or LEDs 60 transmitting light, such as infrared light. The optical sensors 50 preferably have sampling rates of 100 Hz or more, more preferably 300 Hz or more, and most preferably 500 Hz or more. In some embodiments, the optical sensors 50 have sampling rates of 8000 Hz. The sampling rate is the rate at which the optical sensors 50 receive light signals from sequentially fired LEDs 60. In some embodiments, the light signals from the LEDs 60 are fired at different rates for each tracker 54, 56, 58.

Figure 2:
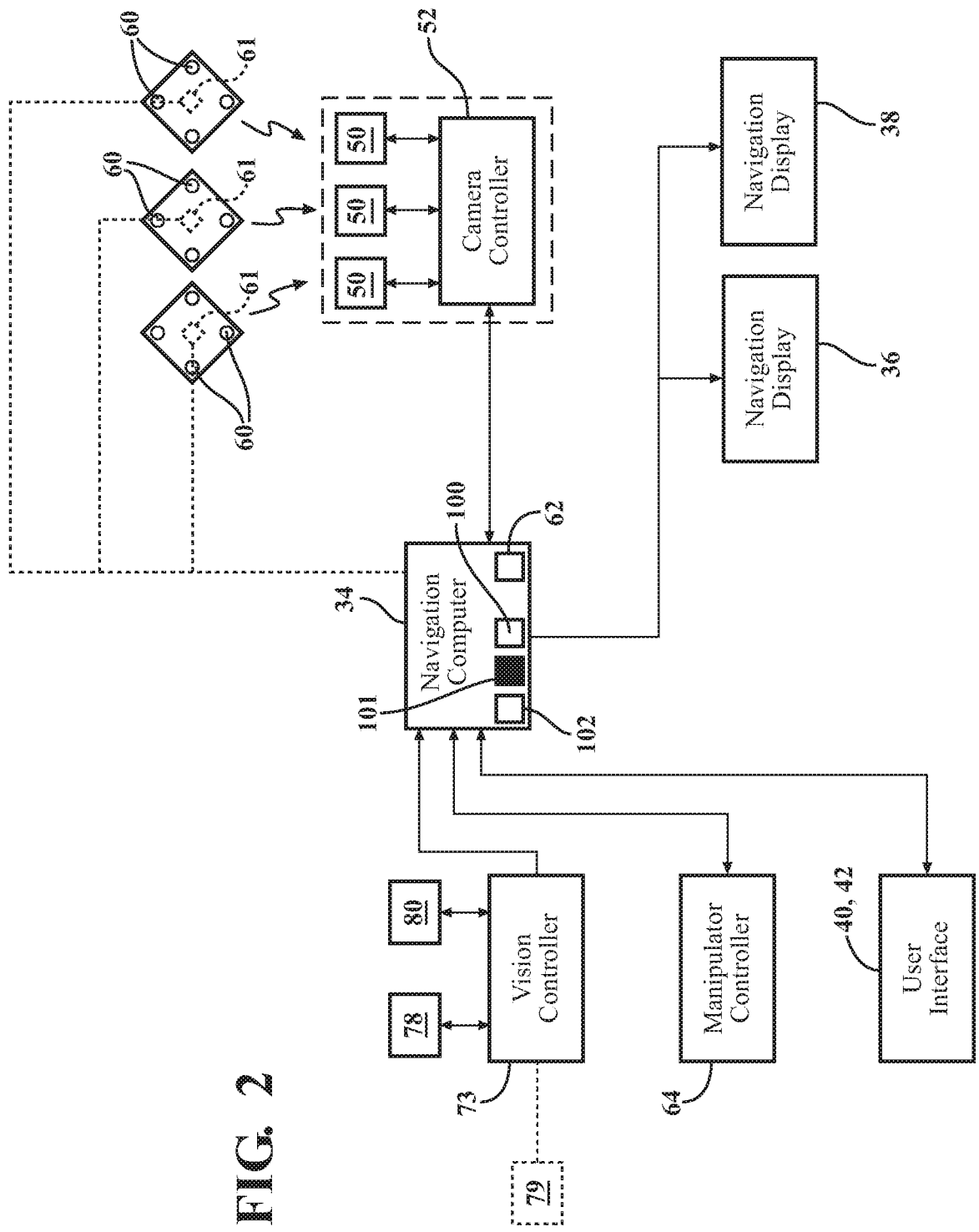
FIG. 2 is a schematic view of a control system for controlling the robotic surgical system.

Referring to FIG. 2, each of the LEDs 60 are connected to a tracker controller 61 located in a housing of the associated tracker 54, 56, 58 that transmits/receives data to/from the navigation computer 34. In one embodiment, the tracker controllers 61 transmit data on the order of several Megabytes/second through wired connections with the navigation computer 34. In other embodiments, a wireless connection may be used. In these embodiments, the navigation computer 34 has a transceiver (not shown) to receive data from the tracker controller.

In other embodiments, the trackers 54, 56, 58 may have passive markers (not shown), such as reflectors that reflect light emitted from the localizer camera unit 46. The reflected light is then received by the optical sensors 50. Active and passive arrangements are well known in the art.

In some embodiments, the trackers 54, 56, 58 also include a gyroscope sensor and accelerometer, such as the trackers shown in U.S. Pat. No. 9,008,757 to Wu, issued on Apr. 14, 2015, entitled "Navigation System Including Optical and Non-Optical Sensors," hereby incorporated by reference.

The navigation computer 34 includes the navigation processor 62. It should be understood that the navigation processor 62 could include one or more processors to control operation of the navigation computer 34. The processors can be any type of microprocessor or multi-processor system. The term processor is not intended to limit the scope of any embodiment to a single processor.

The localizer camera unit 46 receives optical signals from the LEDs 60 of the trackers 54, 56, 58 and outputs to the navigation processor 62 signals relating to the position of the LEDs 60 of the trackers 54, 56, 58 relative to the localizer 44. Based on the received optical (and non-optical signals in some embodiments), navigation processor 62 generates data indicating the relative positions and orientations of the trackers 54, 56, 58 relative to the localizer 44, such as through known triangulation methods. In some embodiments, the data is generated by the localizer camera controller 52 and then transmitted to the navigation computer 34.

Prior to the start of the surgical procedure, additional data are loaded into the navigation processor 62. Based on the position and orientation of the trackers 54, 56, 58 and the previously loaded data, navigation processor 62 determines the position of the treatment end of the surgical instrument 30 (e.g., the centroid of a surgical bur) and the orientation of the surgical instrument 30 relative to the target sites against which the treatment end is to be applied, such as the femur target site TS. In some embodiments, navigation processor 62 forwards these data to a manipulator controller 64. The manipulator controller 64 can then use the data to control the manipulator 66 as described in U.S. Pat. No. 9,119,655, entitled, "Surgical Manipulator Capable of Controlling a Surgical Instrument in Multiple Modes," the disclosure of which is hereby incorporated by reference. In one embodiment, the manipulator 66 is controlled with respect to the virtual objects set by the surgeon. In the embodiment described herein, the virtual object VB defines the volume of material of the femur F to be removed by the surgical instrument 30. Thus, the virtual object VB provides a virtual boundary for the treatment end of the surgical instrument 30 to stay within (i.e., for a separate virtual object associated with the treatment end of the surgical instrument to stay within).

The navigation processor 62 also generates image signals that indicate the relative position of the treatment end to the target sites. These image signals are applied to the displays 36, 38. Displays 36, 38, based on these signals, generate images that allow the surgeon and staff to virtually view the relative position of the treatment end to the target sites. In most cases, the images illustrate the treatment end with respect to one target site at a time. For instance, in a surgical procedure in which the femur F and the tibia T are both being treated, the femur target site TS and the relative position of the treatment end of the surgical instrument 30 to the femur target site TS may be visually represented while material is being removed from the femur F. Likewise, when the user is finished removing material from the femur F and is ready to remove material from the tibia T, the display 36, 38 may only illustrate placement of the treatment end of the surgical instrument 30 with respect to the target site associated with the tibia T.

Figure 3:
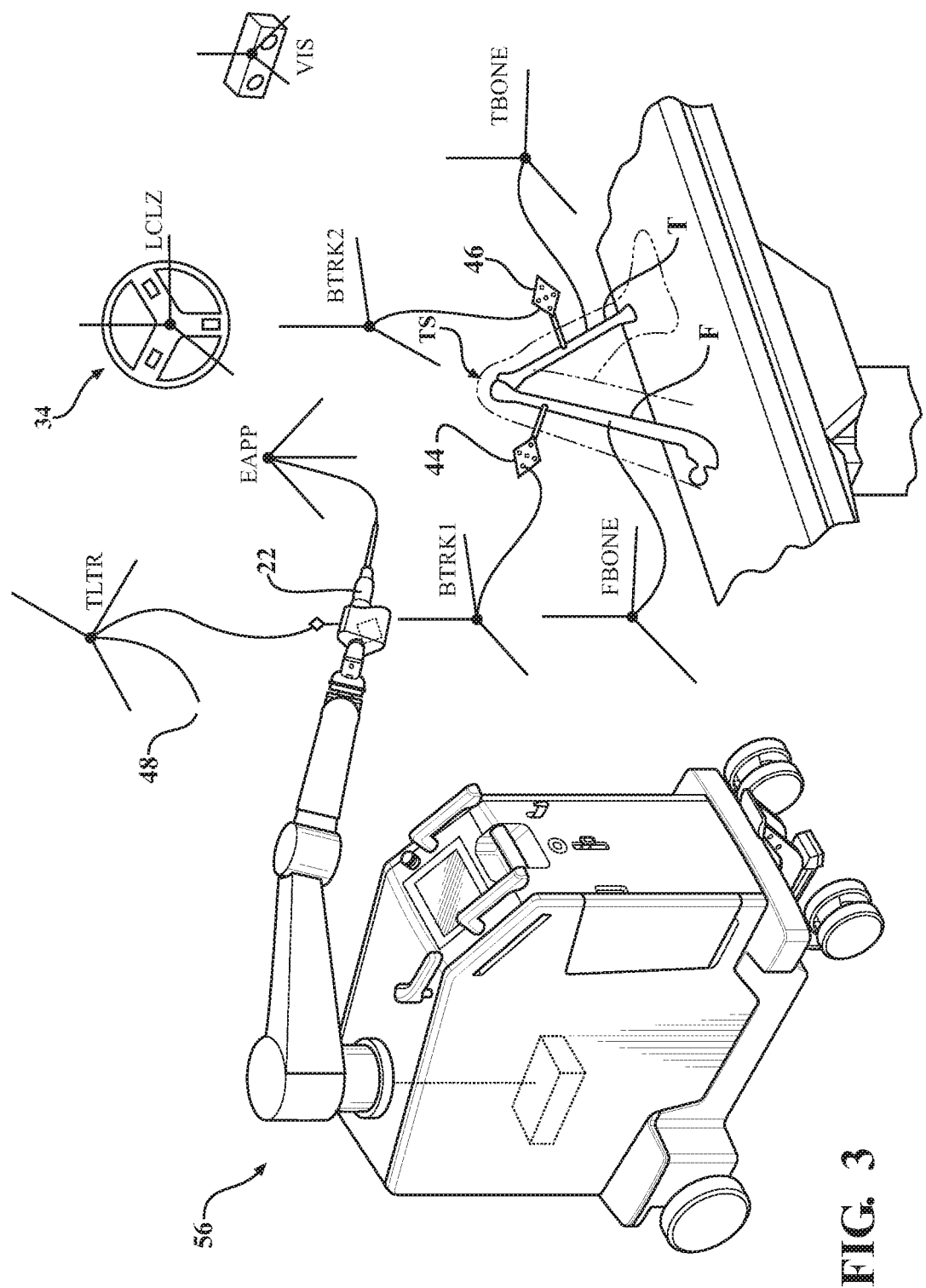
FIG. 3 is a perspective view of coordinate systems used in the robotic surgical system.

Referring to FIG. 3, tracking of objects is generally conducted with reference to a localizer coordinate system LCLZ. The localizer coordinate system LCLZ has an origin and an orientation (a set of x, y, and z axes). During the procedure one goal is to keep the localizer coordinate system LCLZ in a known position. An accelerometer (not shown) mounted to the localizer camera unit 46 may be used to track sudden or unexpected movement of the localizer coordinate system LCLZ, as may occur when the localizer camera unit 46 is inadvertently bumped by surgical personnel.

Each tracker 54, 56, 58, and object being tracked also has its own coordinate system separate from the localizer coordinate system LCLZ. For instance, the trackers 54, 56, 58 have bone tracker coordinate system BTRK1, bone tracker coordinate system BTRK2, and instrument tracker coordinate system TLTR.

In the embodiment shown, the guidance station 26 monitors the positions of the femur F and tibia T of the patient by monitoring the position of bone trackers 54, 56 firmly attached to bone. Femur coordinate system is FBONE and tibia coordinate system is TBONE, which are the coordinate systems of the bones to which the bone trackers 54, 56 are firmly attached.

Prior to the start of the procedure, pre-operative images of the anatomy of interest are generated, such as pre-operative images of the femur F and tibia T (or of other tissues or structures in other embodiments). These images may be based on MRI scans, radiological scans or computed tomography (CT) scans of the patient's anatomy. These images are used to develop virtual models of anatomy of interest, such as virtual models of the femur F and tibia T and/or other anatomy to be treated by the surgical instrument 30. Often the virtual models are 3-D models that comprise data representing the entire anatomy being treated or at least a portion of the anatomy to be treated and data representing the virtual objects that define the target sites. In the embodiment shown, a virtual model VM of the femur is a 3-D model comprising model data that represents a portion of the femur F and the virtual object VB (see FIG. 4). The virtual object VB defines the target site TS and the volume of material to be removed from the femur F during the surgical procedure. The virtual objects may be defined within the virtual models and may be represented as mesh surfaces, constructive solid geometries (CSG), voxels, or using other virtual object representation techniques.

The pre-operative images and/or the virtual models are mapped to the femur coordinate system FBONE and tibia coordinate system TBONE using well known methods in the art. These pre-operative images and/or virtual models are fixed in the femur coordinate system FBONE and tibia coordinate system TBONE. As an alternative to taking pre-operative images, plans for treatment can be developed in the operating room from kinematic studies, bone tracing, and other methods. These same methods could also be used to generate the 3-D virtual models previously described.

During an initial phase of the procedure described herein, the bone trackers 54, 56 are firmly affixed to the bones of the patient. The pose (position and orientation) of coordinate systems FBONE and TBONE are mapped to coordinate systems BTRK1 and BTRK2, respectively. In one embodiment, a pointer instrument P (see FIG. 1), such as disclosed in U.S. Pat. No. 7,725,162 to Malackowski, et al., hereby incorporated by reference, having its own tracker PT (see FIG. 1), may be used to register the femur coordinate system FBONE and tibia coordinate system TBONE to the bone tracker coordinate systems BTRK1 and BTRK2, respectively. Given the fixed relationship between the bones and their trackers 54, 56, positions and orientations of the femur F and tibia T in the femur coordinate system FBONE and tibia coordinate system TBONE can be transformed to the bone tracker coordinate systems BTRK1 and BTRK2 so the localizer camera unit 46 is able to track the femur F and tibia T by tracking the trackers 54, 56. These pose-describing data are stored in memory integral with both the manipulator controller 64 and the navigation processor 62.

The treatment end of the surgical instrument 30 (also referred to as a distal end of an energy applicator) has its own coordinate system EAPP. The origin of the coordinate system EAPP may represent a centroid of a surgical cutting bur, for example. The pose of coordinate system EAPP is fixed to the pose of instrument tracker coordinate system TLTR before the procedure begins. Accordingly, the poses of these coordinate systems EAPP, TLTR relative to each other are determined. The pose-describing data are stored in memory integral with manipulator controller 64 and navigation processor 62.

Referring to FIG. 2, a localization engine 100 is a software module that can be considered part of the navigation computer 34. Components of the localization engine 100 run on navigation processor 62. The localization engine 100 may run on the manipulator controller 64 and/or the navigation processor 62.

Localization engine 100 receives as inputs the optically-based signals from the localizer camera controller 52 and, in some embodiments, the non-optically based signals from the tracker controller (not shown). Based on these signals, localization engine 100 determines the pose of the bone tracker coordinate systems BTRK1 and BTRK2 in the localizer coordinate system LCLZ. Based on the same signals received for the instrument tracker 58, the localization engine 100 determines the pose of the instrument tracker coordinate system TLTR in the localizer coordinate system LCLZ.

The localization engine 100 forwards the signals representative of the poses of trackers 54, 56, 58 to a coordinate transformer 102. Coordinate transformer 102 is a software module that runs on navigation processor 62. Coordinate transformer 102 references the data that defines the relationship between the pre-operative images and/or the virtual models of the patient and the bone trackers 54, 56. Coordinate transformer 102 also stores the data indicating the pose of the treatment end of the surgical instrument 30 relative to the instrument tracker 58. Coordinate transformer 102 also references the data that defines the virtual objects, if separate from the virtual models.

During the procedure, the coordinate transformer 102 receives the data indicating the relative poses of the trackers 54, 56, 58 to the localizer 44. Based on these data and the previously loaded data, the coordinate transformer 102 generates data indicating the relative position and orientation of both the coordinate system EAPP, and the bone coordinate systems, FBONE, TBONE to the localizer coordinate system LCLZ.

As a result, coordinate transformer 102 generates data indicating the position and orientation of the treatment end of the surgical instrument 30 relative to the target sites against which the treatment end is applied. Image signals representative of these data are forwarded to displays 36, 38 enabling the surgeon and staff to view this information. In certain embodiments, other signals representative of these data can be forwarded to the manipulator controller 64 to guide the manipulator 66 and corresponding movement of the surgical instrument 30. Thus, this data also indicates a virtual location of the treatment end of the surgical instrument 30, which may also be modeled as a separate virtual object, with respect to the virtual models and the virtual objects.

Referring back to FIG. 1, the guidance station 26 further includes a vision device 72. In the embodiment shown, the vision device is mounted to the localizer camera unit 46. In other embodiments, the vision device 72 may be mounted on a separate adjustable arm to position the vision device 72 separately from the localizer camera unit 46. The vision device 72 is preferably placed with a field of view of the target sites free from obstructions. The vision device 72 has a vision controller 73 in operative communication with the navigation computer 34. The vision device 72 may also be referred to as an imaging device or a digital imaging device capable of capturing 3-D images in real-time. One example of a suitable vision device is the commercially available Kinect SDK or similar Kinect model, sold by Microsoft Corporation. In other embodiments, the vision device 72 may comprise a laser array or a stereo camera system.

The vision device 72 has an outer housing 76 that supports one or more image sensors 78, 79. One of the image sensors may be a depth image sensor 78 used to identify a depth image, while the other image sensor may be a color image sensor 79 used to generate color images. Both image sensors 78, 79 may be in the form of CMOS sensors or other suitable sensors. Additionally, a light source 80 is supported in the housing 76 to generate and transmit light that is reflected back by surfaces in the field of view of the depth image sensor 78.

The sensors 78, 79 and the light source 80 communicate with the vision controller 73 to determine the distances of the surfaces in the field of view with respect to a vision coordinate system VIS (see FIG. 3). In one embodiment the light source 80 emits infrared light and the vision controller 73 determines the elapsed time required for the infrared light to reflect off the surfaces in the field of view and return to the depth image sensor 78. This process is repeated over a plurality of iterations to determine distances from the vision device 72 to surfaces in the field of view of the vision device 72 so that a point cloud 202 can be generated (see FIG. 4).

The navigation computer 34 communicates with the vision controller 73 to receive signals and/or data representative of the point cloud 202. Imaging software, comprising an image generator module, is loaded on the navigation computer 34 and run by the navigation processor 62 to create the point cloud 202 based on the field of view of the vision device 72. The point cloud 202 is created in the vision coordinate system VIS. The point cloud 202 is a set of image data points in the vision coordinate system VIS that correspond to the surfaces in the field of view of the vision device 72. These image data points are defined by x, y, z coordinates. The point cloud 202 can be saved or stored as an image data file.

It should be appreciated that by integrating the vision device 72 into the localizer camera unit 46, the vision coordinate system VIS can be easily registered to the localizer coordinate system LCLZ since the location of the image sensors 78, 79 relative to the optical sensors 50, and vice versa, is known and fixed. During manufacturing the vision device 72 can be calibrated to the localizer 44 to generate data with respect to the same coordinate system so that the vision coordinate system VIS does not need to be transformed to the localizer coordinate system LCLZ via the coordinate transformer 102.

In other embodiments, such as those in which the vision device 72 is separate from the localizer camera unit 46, the vision device 72 may have a tracker (not shown) rigidly mounted to the housing 76 to establish a relationship between the vision coordinate system VIS and the localizer coordinate system LCLZ. For instance, using preloaded data defining a relationship between the tracker's coordinate system and the vision coordinate system VIS, the coordinate transformer 102, based on the position of the tracker in the localizer coordinate system LCLZ, could transform the vision coordinate system VIS to the localizer coordinate system LCLZ.

Figure 4:
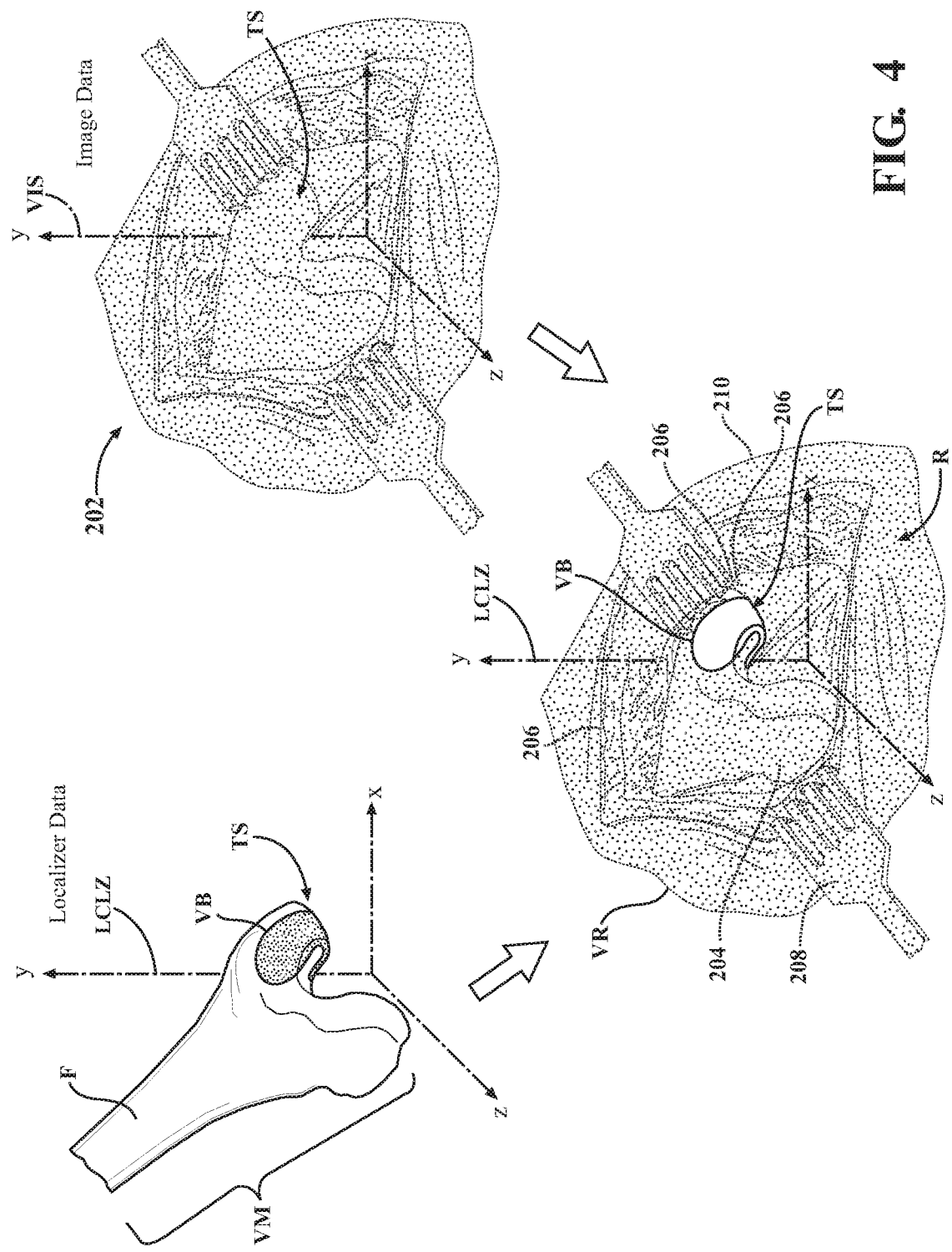
FIG. 4 is an illustration of image data from the vision device being combined with localizer data from the localizer to yield a virtual object defining a region to be avoided.

Referring to FIG. 4, the vision device 72 collects images of the target sites and the surfaces surrounding the target sites that are in the field of view of the vision device 72. In the embodiment shown, the vision device 72 collects images of the target site TS and the surfaces surrounding the target site TS that are in the field of view of the vision device 72. The navigation computer 34 cooperates with the vision controller 73 to create the point cloud 202 of the target site TS and the surfaces surrounding the target site TS, which defines image data associated with the target site TS and the surfaces surrounding the target site TS.

At the same time that the image data is being generated, the localizer data is also being generated. The navigation computer 34 cooperates with the localizer 44 to determine a position and orientation of the virtual models and the virtual objects defining the target sites in the localizer coordinate system LCLZ. In the embodiment shown, the navigation computer 34 cooperates with the localizer 44 to determine a position and orientation of the virtual model VM of the femur F and the position and orientation of the virtual object VB in the localizer coordinate system LCLZ. This localizer data comprises the model data defining the virtual model VM and the virtual object VB. In some cases, the model data includes data points in the form of a point cloud associated with the virtual model VM and a separate point cloud associated with the virtual object VB.

Still referring to FIG. 4, the navigation processor 62 runs a data merge module 101 (see FIG. 1), which is a software module that merges the localizer data and the image data to yield merged data (once the localizer data and the image data is located in, or transformed to, a common coordinate system). The merged data represents a second virtual object VR that defines a region R to be avoided during the surgery that is outside of the target site TS. This merging of data is illustrated by arrows in FIG. 4. In the embodiment shown, the merged data that represents the second virtual object VR may comprise: (1) data points 204 associated with bone that is to be avoided by the surgical instrument 30 that is outside of the target site TS; (2) data points 206 associated with exposed soft tissue that is to be avoided by the surgical instrument 30 that is outside of the target site TS; (3) data points 208 associated with retractors that are to be avoided by the surgical instrument 30; and (4) data points 210 associated with skin of the patient that is outside of the target site TS.

In some embodiments, like that shown in FIG. 4, the merged data comprises all data points in the point cloud 202 that have coordinates located outside of the virtual object VB after the localizer data and the image data are merged. In some cases, when a path for the treatment end of the surgical instrument 30 to reach the target site TS is not completely clear, such as when the target site TS is at least partially obstructed by soft tissue or other sensitive anatomical structures, defining all visible surfaces outside of the target site TS as part of the second virtual object VR can be particularly advantageous so that the surgical instrument 30 is able to avoid any sensitive anatomical structures, tools, etc., that are located outside of the target site TS.

The merged data that represents the second virtual object VR, and which defines the region R to be avoided, can be processed by the navigation processor 62 so that a representation thereof can be displayed to the user on the displays 38, 39 and the user can visualize a position and orientation of the surgical instrument 30 relative to the region R. In some cases, the data points that virtually define the region R to be avoided can be converted into a mesh surface, a constructive solid geometry (CSG), voxels, or other virtual object types using various virtual object representation techniques. Additionally, the navigation processor 62 may automatically limit the size of the second virtual object VR, and thus the extent of the region R, to a predefined distance from the target site TS, or the user may be able to manually refine the second virtual object VR, including defining an outer perimeter of the second virtual object VR.

It should be noted that the second virtual object VR may change in configuration (e.g., size, shape, position, etc.) during the surgical procedure owing to the elastic and/or flexible nature of some of the tissues in the region R defined by the second virtual object VR. Additionally, the region R may change as retractors are adjusted, or as additional tools or equipment are brought into and out of the field of view of the vision device 72. In other words, the nature of the region R to be avoided is dynamic and may continuously change, but with the navigation techniques described herein, the second virtual object VR can be continuously updated (e.g., at a predefined frequency) with each new set of image data and localizer data so that the user is able to avoid the region R to be avoided during the surgical procedure regardless of changes to the region R.

The second virtual object VR that defines the region R to be avoided can also be transmitted to the manipulator controller 64 and treated as a "no-fly" zone in which the treatment end of the surgical instrument 30 is prevented from entering. As a result, when the manipulator 66 operates in an autonomous mode, the manipulator 66 is able to control positioning of the surgical instrument 30 to avoid the region R and thereby avoid sensitive anatomical structures, such as soft tissue and bone to be preserved, and tools, such as retractors, suction tubes, and the like, located near the target site TS.

Figure 5:
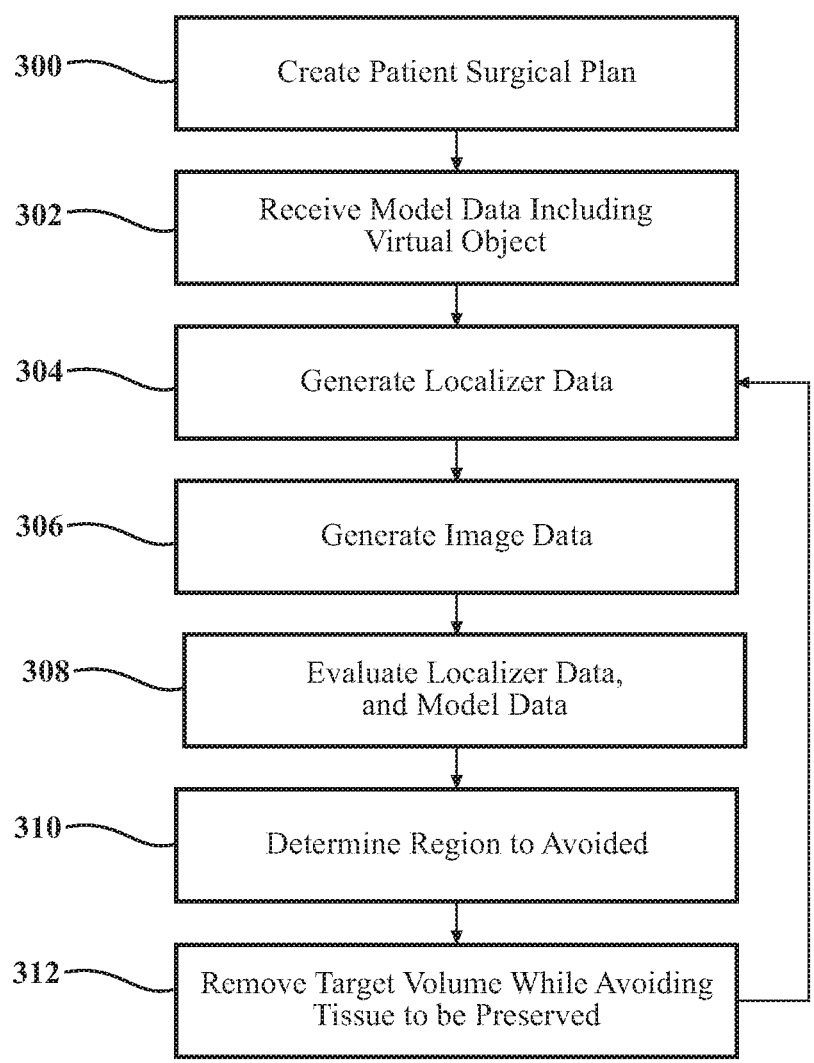
FIG. 5 is a flow chart of steps carried out by a method of treating the patient.

Referring to FIG. 5, one embodiment of a method for determining the region R to be avoided is shown. In step 300, a surgeon or other medical professional creates a surgical plan for the patient. The surgical plan identifies the surgical procedure to be performed and the treatment to be undertaken. The surgical plan is often based on pre-operative images, such as images taken from MRI or CT scans, which are converted into a 3-D virtual model VM of the patient's anatomy. The virtual object VB defining the target site TS to be treated during the surgical procedure is also generated and associated with the 3-D virtual model VM as part of the surgical plan.

In step 302, data relating to the virtual model VM and the virtual object VB, which defines the target volume of material to be treated at the target site TS, such as the target volume of bone to be removed, are transferred to the navigation computer 34 to be stored in the navigation computer 34.

In step 304, localizer data is then generated. The localizer data comprises data associated with the positions and orientations of the virtual model VM and the virtual object VB in the localizer coordinate system LCLZ. Image data is simultaneously being generated in step 306 so that at each time step during navigation, there is corresponding localizer data and image data. The image data comprises the point cloud 202 which comprises the position and orientation of surfaces in the field of view of the vision device 72, including surfaces of the target site TS and surfaces outside of the target site TS.

In step 308, the data merge module 101 of the navigation computer 34 evaluates the localizer data and the image data. In particular, the data merge module 101 merges data points from the image data (e.g., the point cloud 202) with data points from the localizer data (e.g., data points for the virtual object VB). In step 310, the data merge module 101 then identifies all of the data points from the image data that fall outside of the virtual object VB. This remaining data set yields the region R to be avoided, which is then saved in memory in the navigation computer 34 as the second virtual object VR to be avoided by the surgical instrument 30. In step 312, the user operates the surgical instrument 30, either manually, or robotically, to remove the target volume of tissue from the target site, while avoiding the region R. The steps 304-312 repeat for each processing time step during navigation until the surgical procedure is complete, e.g., until all the tissue has been removed from the target site TS. As a result, the method is able to compensate for changes to the region R during the surgical procedure.

In other embodiments, it should be appreciated that the systems and methods described herein for merging localizer data and image data could similarly be performed to generate other types of virtual objects, other than virtual objects that define regions to be avoided, like the region R. For instance, the localizer data and the image data could be merged to yield virtual objects that define target sites, such as volumes of material to be removed, desired trajectories for the surgical instrument 30, and the like. Additionally, the image data and the localizer data could be merged for other purposes.

As will be appreciated by one skilled in the art, aspects of the present embodiments may take the form of a computer program product embodied in one or more computer readable medium(s) having computer readable program code embodied thereon. Computer software including instructions or code for performing the methodologies described herein, may be stored in one or more of the associated memory devices (for example, ROM, fixed or removable memory) and, when ready to be utilized, loaded in part or in whole (for example, into RAM) and implemented by a CPU. Such software could include, but is not limited to, firmware, resident software, microcode, and the like.

Several embodiments have been discussed in the foregoing description. However, the embodiments discussed herein are not intended to be exhaustive or limit the invention to any particular form. The terminology which has been used is intended to be in the nature of words of description rather than of limitation. Many modifications and variations are possible in light of the above teachings and the invention may be practiced otherwise than as specifically described.

What is claimed is:

1. A surgical navigation system for performing surgery at a target site on a patient, the target site defined by a virtual object, said system comprising:
    a patient tracker configured to be attached to the patient;
    a localizer configured to cooperate with said patient tracker to generate localizer data associated with the target site;
    a vision device configured to generate, in a coordinate system of said vision device, image data associated with the target site and surfaces surrounding the target site;
    a navigation computer coupled to said localizer and said vision device, and said navigation computer being configured to:
        determine a position and orientation of said virtual object in a coordinate system of said localizer based on said localizer data;
        combine said localizer data and said image data into a common coordinate system;
        merge said localizer data and said image data to identify data points in said image data that have coordinates located outside of said virtual object; and
        associate a second virtual object with said identified data points in said image data that have coordinates located outside of said virtual object, wherein said second virtual object defines a region outside of the target site that is to be avoided.

2. The system as set forth in claim 1 wherein said image data generated by said vision device comprises a three dimensional map of at least a portion of the surfaces surrounding the target site that are outside of the target site.

3. The system as set forth in claim 2 wherein said three dimensional map comprises one or more of a point cloud, a range map, a plane, a line, or a single point.

4. The system as set forth in claim 1 wherein said virtual object further defines a volume of material to be removed from the target site.

5. A robotic surgical system for performing surgery at a target site on a patient, the target site defined by a virtual object, said system comprising:
a robotic device;
an end effector coupled to said robotic device and configured to treat the patient at the target site;
a patient tracker configured to be attached to the patient;
a localizer configured to cooperate with said patient tracker to generate localizer data associated with the target site;
a vision device configured to generate, in a coordinate system of said vision device, image data associated with the target site and surfaces surrounding the target site; and
a navigation computer coupled to said localizer and said vision device, and said navigation computer being configured to:
determine a position and orientation of said virtual object in a coordinate system of said localizer based on said localizer data;
combine said localizer data and said image data into a common coordinate system;
merge said localizer data and said image data to identify data points in said image data that have coordinates located outside of said virtual object;
associate a second virtual object with said identified data points in said image data that have coordinates located outside of said virtual object, wherein said second virtual object defines a region outside of the target site that is to be avoided; and
wherein said navigation computer is coupled to said robotic device so that said robotic device is operable to move said end effector with respect to the target site while avoiding the region outside of the target site that is to be avoided.

6. The robotic surgical system as set forth in claim 5, wherein said virtual object further defines a volume of material to be removed from the target site by said end effector, and wherein said robotic device is operable to move said end effector such that movement of said end effector with respect to the target site is constrained to stay within said virtual object.

7. A method for performing surgery at a target site defined by a virtual object, utilizing a patient tracker attached to a patient, a localizer, a vision device, and a navigation computer coupled to the localizer and the vision device, said method comprising:
generating, with the localizer, localizer data associated with the target site while the patient tracker is attached to the patient;
generating, with the vision device and in a coordinate system of the vision device, image data associated with the target site and surfaces surrounding the target site;
determining, with the navigation computer, a position and orientation of the virtual object in a coordinate system of the localizer based on the localizer data;
combining, with the navigation computer, the localizer data and the image data into a common coordinate system;
merging, with the navigation computer, the localizer data and the image data to identify data points in the image data that have coordinates located outside of the virtual object; and
associating, with the navigation computer, a second virtual object with the identified data points in the image data that have coordinates located outside of the virtual object, wherein the second virtual object defines a region outside of the target site that is to be avoided.

8. The method as set forth in claim 7, wherein generating the image data associated with the target site and surfaces surrounding the target site comprises generating a three dimensional map of at least a portion of the surfaces surrounding the target site that are outside of the target site.

9. The method as set forth in claim 8, wherein generating the three dimensional map of the at least a portion of the surfaces surrounding the target site that are outside of the target site comprises generating one or more of a point cloud, a range map, a plane, a line, or a single point.

10. The method as set forth in claim 7 wherein the virtual object further defines a volume of material to be removed from the target site.

11. A method for performing robotic surgery at a target site defined by a virtual object, utilizing a patient tracker attached to a patient, a localizer, a vision device, an end effector attached to a robotic device, and a navigation computer coupled to the localizer, the vision device, and the robotic device, said method comprising:
generating, with the localizer, localizer data associated with the target site while the patient tracker is attached to the patient;
generating, with the vision device and in a coordinate system of the vision device, image data associated with the target site and surfaces surrounding the target site;
determining, with the navigation computer, a position and orientation of the virtual object in a coordinate system of the localizer based on the localizer data;
combining, with the navigation computer, the localizer data and the image data into a common coordinate system;
merging, with the navigation computer, the localizer data and the image data to identify data points in the image data that have coordinates located outside of the virtual object;
associating, with the navigation computer, a second virtual object with the identified data points in the image data that have coordinates located outside of the virtual object, wherein the second virtual object defines a region outside of the target site that is to be avoided; and
moving, with the robotic device, the end effector with respect to the target site while avoiding the region outside of the target site that is to be avoided.

12. The method as set forth in claim 11, wherein the virtual object further defines a volume of material to be removed from the target site by the end effector, and wherein the robotic device is operable to move the end effector such that movement of the end effector with respect to the target site is constrained to stay within said virtual object.

* * * * *